(12) United States Patent
Hirota

(10) Patent No.: US 10,891,743 B2
(45) Date of Patent: Jan. 12, 2021

(54) IMAGE PROCESSING DEVICE, OPERATION METHOD PERFORMED BY IMAGE PROCESSING DEVICE AND COMPUTER READABLE RECORDING MEDIUM FOR PERFORMING DIFFERENT ENHANCEMENT PROCESSINGS BASED ON CONTEXT OF UPDATE DETERMINED FROM LATEST IMAGE ACQUIRED

(71) Applicant: OLYMPUS CORPORATION, Tokyo (JP)

(72) Inventor: Masashi Hirota, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 96 days.

(21) Appl. No.: 16/218,831

(22) Filed: Dec. 13, 2018

(65) Prior Publication Data

US 2019/0114792 A1    Apr. 18, 2019

Related U.S. Application Data

(63) Continuation of application No. PCT/JP2016/068540, filed on Jun. 22, 2016.

(51) Int. Cl.
*G06K 9/00* (2006.01)
*G06T 7/33* (2017.01)
(Continued)

(52) U.S. Cl.
CPC .......... *G06T 7/337* (2017.01); *A61B 1/00009* (2013.01); *G06F 9/30003* (2013.01);
(Continued)

(58) Field of Classification Search
CPC ..................................................... G06K 9/2018
See application file for complete search history.

(56) References Cited

U.S. PATENT DOCUMENTS 4,961,110 A * 10/1990 Nakamura ......... H04N 9/04521
348/70
8,212,892 B2    7/2012 Yamazaki
(Continued)

FOREIGN PATENT DOCUMENTS

EP    2474265 A2 *   7/2012  ............. A61B 1/043
EP    2700349 A1 *   2/2014  ............. G06T 5/009
(Continued)

OTHER PUBLICATIONS

Appearance of enhanced tissue features in narro-band endoscopic imaging, Kazuhiro Gono et al., Journal of Biomedical optics, 2004, pp. 568-577 (Year: 2004).*
(Continued)

*Primary Examiner* — Jayesh A Patel
(74) *Attorney, Agent, or Firm* — Scully, Scott, Murphy & Presser, P.C.

(57) ABSTRACT

An image processing device is configured to perform enhancement processing on a specific image, using multiple images of types that are different from one another at least one of which is captured at a time different from a time at which other images are captured. The image processing device includes a processor comprising hardware, the processor being configured to execute: acquiring the multiple images; calculating information representing a state of at least one of the multiple images that is used for enhancement; and creating an enhanced image by performing the enhancement processing on an image to be enhanced based on the information representing the state and the multiple images.

16 Claims, 15 Drawing Sheets

(51) Int. Cl.
G06T 5/50 (2006.01)
G06K 9/20 (2006.01)
G06K 9/03 (2006.01)
A61B 1/00 (2006.01)
G06F 9/30 (2018.01)
G06K 9/46 (2006.01)

(52) U.S. Cl.
CPC ........... G06K 9/036 (2013.01); G06K 9/2018 (2013.01); G06K 9/46 (2013.01); G06T 5/50 (2013.01)

(56) References Cited

U.S. PATENT DOCUMENTS

| | | | |
|---|---|---|---|
| 9,277,190 B2 | 3/2016 | Igarashi et al. | |
| 9,918,613 B2* | 3/2018 | Saito | A61B 1/00009 |
| 10,039,439 B2* | 8/2018 | Aoyama | H04N 5/2256 |
| 2003/0016856 A1* | 1/2003 | Walker | G06T 1/00 382/132 |
| 2007/0140538 A1* | 6/2007 | Doran | G06F 19/321 382/128 |
| 2008/0165247 A1* | 7/2008 | Beresford | G06K 9/38 348/65 |
| 2012/0154566 A1 | 6/2012 | Kaku | |
| 2012/0190922 A1* | 7/2012 | Kaku | A61B 1/0005 600/109 |
| 2012/0220824 A1* | 8/2012 | Kaku | A61B 1/0653 600/109 |
| 2013/0083180 A1* | 4/2013 | Sasaki | H04N 5/23212 348/65 |
| 2014/0292793 A1* | 10/2014 | Lai | G09G 5/10 345/589 |
| 2015/0099932 A1 | 4/2015 | Morimoto et al. | |
| 2015/0363932 A1* | 12/2015 | Hirota | A61B 1/041 382/128 |
| 2019/0038111 A1* | 2/2019 | Endo | A61B 1/00009 |
| 2019/0052793 A1* | 2/2019 | Vink | H04N 5/232133 |

FOREIGN PATENT DOCUMENTS

| | | |
|---|---|---|
| JP | 2012125461 A | 7/2012 |
| JP | 5362149 B1 | 12/2013 |
| JP | 2014161639 A | 9/2014 |
| JP | 2015047402 A | 3/2015 |
| JP | 2015070946 A | 4/2015 |
| WO | 2010131620 A1 | 11/2010 |
| WO | 2013145409 A1 | 10/2013 |

OTHER PUBLICATIONS

Narro-Band imaging in digestive Endoscopy, R Lambert et al., The sceintific world Journal, 2007, pp. 449-465 (Year: 2007).*

Narrow Band Imaging: Technology Basis—History., Kazuhiro Gono., Clinical Endoscopy, 2015, pp. 476-480 (Year: 2015).*

International Search Report dated Sep. 13, 2016 issued in PCT/JP2016/068540.

* cited by examiner

IMAGE PROCESSING DEVICE, OPERATION METHOD PERFORMED BY IMAGE PROCESSING DEVICE AND COMPUTER READABLE RECORDING MEDIUM FOR PERFORMING DIFFERENT ENHANCEMENT PROCESSINGS BASED ON CONTEXT OF UPDATE DETERMINED FROM LATEST IMAGE ACQUIRED

CROSS-REFERENCE TO RELATED APPLICATION

This application is a continuation of International Application No. PCT/JP2016/068540, filed on Jun. 22, 2016, the entire contents of which are incorporated herein by reference.

BACKGROUND

The present disclosure relates to an image processing device, an operation method performed by the image processing device, and a computer readable recording medium.

White light and narrow-band light are used as illumination light to illuminate the inside of a living body with an endoscope. As the absorption and scattering characteristics of narrow-band light differs depending on the wavelength band, appropriate choice of narrowband light to be used enables extraction of characteristics of an object corresponding to the wavelength band. In the related art, a process to enhance specific information based on multiple images using such a difference in absorption and scattering characteristics has been proposed.

For example, Japanese Patent No. 5362149 discloses a technique in which two images with different light absorption characteristics of hemoglobin are used and a change in absorption of light in one of the images is enhanced.

SUMMARY

An image processing device according to one aspect of the present disclosure is configured to perform enhancement processing on a specific image, using multiple images of types that are different from one another at least one of which is captured at a time different from a time at which other images are captured, and includes a processor comprising hardware, the processor being configured to execute: acquiring the multiple images; calculating information representing a state of at least one of the multiple images that is used for enhancement; and creating an enhanced image by performing the enhancement processing on an image to be enhanced based on the information representing the state and the multiple images.

The above and other features, advantages and technical and industrial significance of this disclosure will be better understood by reading the following detailed description of presently preferred embodiments of the disclosure, when considered in connection with the accompanying drawings.

DETAILED DESCRIPTION

Image processing devices, operation methods each performed by an image processing device and operation programs each for an image processing device according to embodiments will be described with reference to the accompanying drawings. The embodiments do not limit the present disclosure. In description of the drawings, the same components are denoted with the same reference numbers.

First Embodiment

Figure 1:
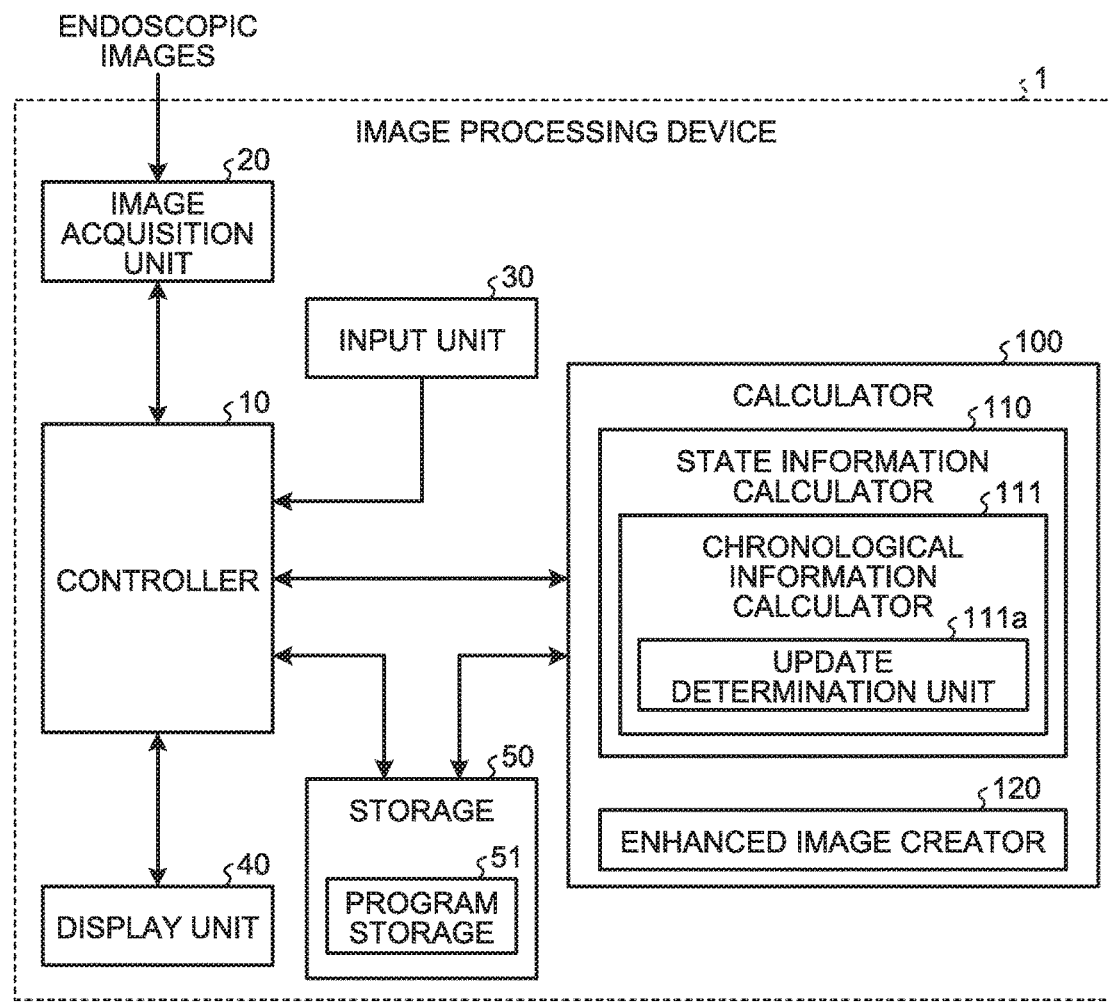
FIG. 1 is a block diagram illustrating a functional configuration of an image processing device according to a first embodiment.

FIG. 1 is a block diagram illustrating a functional configuration of an image processing device according to a first embodiment. An image processing device 1 according to the first embodiment is a device that, based on multiple images that are acquired by an endoscope, extracts a change in absorption of light that hardly appears in white images and synthesizes the extracted change in absorption of light and at least one of the multiple images to create an image to be displayed.

In the following description, endoscopic images including narrow-band images and white images that are acquired by capturing in-vivo images of the lumen of a living body with a general endoscope referred to as video scope or capsule endoscope are processed.

As illustrated in FIG. 1, the image processing device 1 includes a controller 10 that controls entire operations of the image processing device 1; an image acquisition unit 20 that acquires image data of endoscopic images; an input unit 30 that generates an input signal in response to an external operation; a display unit 40 that makes various displays; a storage 50 that stores image data that is acquired by the image acquisition unit 20 and various programs; and a calculator 100 that executes given image processing on image data.

The controller 10 is configured of a general-purpose processor, such as a central processing unit (CPU), or a dedicated processor, including various processing circuits that execute given functions, such as an application specific integrated circuit (ASIC). When the controller 10 is a general-purpose processor, the controller 10 reads the various programs stored in the storage 50 to perform transfer of instructions and data to the components of the image processing device 1, etc., and perform overall control on entire operations of the image processing device 1. When the controller 10 is a dedicate processor, the processor may execute various processes independently or, by using various types of data stored in the storage 50, the processor and the storage 50 may cooperate or be combined to execute various processes.

The image acquisition unit 20 is configured properly according to the mode of the system including the endoscope. For example, when the image acquisition unit 20 is connected to the image processing device 1 of a general-endoscope system with a video scope that is inserted into a body, the image acquisition unit 20 consists of an interface that loads image data that is generated in the endoscopes system. When a server that saves image data that is generated in the endoscope system is set, the image acquisition unit 20 consists of a communication device that is connected to the server, etc., and performs data communication with the server to acquire image data. Alternatively, when a capsule endoscope that captures images while moving through a living body is used, image data may be communicated with the capsule endoscope using a portable storage medium. In this case, the image acquisition unit 20 consists of a reader device on which a portable storage medium is detachably mounted to read image data of images stored therein.

The input unit 30 consists of, for example, an input device including a keyboard, a mouse, a touch panel and various switches and outputs an input signal that is generated according to an external operation on the input device to the controller 10.

The display unit 40 consists of a display device, such as a liquid crystal display (LCD) or a electroluminescence (EL) display, and displays various screens containing endoscopic images under the control of the controller 10.

The storage 50 consists of an information storage device including various IC memories, such as a ROM or a RAM that is an updatable and recordable flash memory, a hard disk that is incorporated or connected by a data communication terminal or a CD-ROM, and a device that writes and reads information in and from the information storage device. The storage 50 stores, in addition to image data of endoscopic images that are acquired by the image acquisition unit 20, a program for causing the image processing device 1 to operate and causing the image processing device 1 to execute various functions, data that is used during execution of the program, etc. Specifically, the storage 50 includes a program storage 51 that stores an operation program for an image processing device 1 that causes the image processing device 1 to execute image processing to create an enhanced image by enhancing one or multiple narrowband images based on multiple narrowband images that are acquired by the endoscope and that have distributions of wavelength components that are different from one another.

The calculator 100 consists of a general-purpose processor, such as a CPU, or a dedicated processor, including various processing circuits that execute given functions, such as an ASIC. When the calculator 100 is a general-purpose processor, the calculator 100 reads an image processing program that is stored in the program storage 51 to execute image processing. When the calculator 100 is a dedicated processor, the processor may execute various types of processing independently or may cooperate or be combined with the storage 50 to execute images processing using various types of data, etc., stored in the storage 50.

The configuration of the calculator 100 will be described. As illustrated in FIG. 1, the calculator 100 includes a state information calculator 110 that calculates state information on an image from multiple narrowband images that are acquired by the image acquisition unit 20; and an enhanced image creator 120 that creates an enhanced image obtained by enhancing a narrowband image based on the state information. A process performed when multiple narrowband images corresponding to center wavelengths that are different from one another are acquired will be described below as an example.

The first embodiment will be described as one where four narrowband lights whose center wavelengths are 415 nm, 460 nm, 540 nm and 630 nm are applied sequentially to acquire narrowband images. It is described herein that multiple narrowband images corresponding to different types of narrowband lights, which are narrowband images acquired using narrowband lights whose center wavelengths are different from one another, are acquired. A narrowband image that is captured using a narrowband light whose center wavelength is X nm will be referred to as a $\lambda_X$ image below. In the first embodiment, all the four narrowband images are used for enhancement and a $\lambda_{540}$ image and information that is extracted based on a $\lambda_{415}$ image, a $\lambda_{460}$ image and a $\lambda_{630}$ image are synthesized to enhance the $\lambda_{540}$ image. The narrowband light around 415 nm is characterized by tending to be absorbed into hemoglobin easily and tending to scatter onto the mucous membrane in the lumen. The narrowband light around 630 nm is characterized by being hardly absorbed into hemoglobin and hardly scattering onto the mucous membrane and thus tending to reach the back of the lumen. As described above, it is possible to, based on the difference in characteristics among the narrowband lights, extract image information, such as a change in areal light absorption caused by microvessels of a surface layer under the mucous membrane and proliferation of blood vessels, as light absorption information from the narrowband images.

The state information calculator 110 performs a process of calculating state information representing the state of a narrowband image used for enhancement. Specifically, the state information calculator 110 determines whether the $\lambda_{540}$ image to be enhanced is the narrowband image in the latest frame and uses the result of the determination as state information. The newly acquired narrowband image is stored in, for example, the storage 50. When an old narrowband image is stored as a narrowband image of the same narrowband, the currently acquired narrowband image is used as the latest narrowband image to update the narrowband image. The state of the narrowband image herein refers to an update state representing whether the narrowband image that is set in advance is updated by the latest narrowband mage.

The state information calculator 110 includes a chronological information calculator 111 that calculates information representing a chronological state of a narrowband image. The chronological information calculator 111 includes an update determination unit 111a that determines an update state of a narrowband image used for enhancement. The chronological state represents whether a narrowband image that is acquired in chronological order is updated and refers to the state of chronological change. The update determination unit 111a determines whether the $\lambda_{540}$ image that is the narrowband image to be enhanced is the narrowband image in the latest frame. The update determination unit 111a will be described below as one that determines whether the narrowband image to be enhanced is newly acquired as the latest narrowband image and the narrow band image is updated.

Based on the state information that is calculated by the state information calculator 110, the enhanced image creator 120 synthesizes the $\lambda_{540}$ image and information that is extracted based on the $\lambda_{415}$ image, the $\lambda_{460}$ image and the $\lambda_{630}$ image, thereby performing enhancement processing on the $\lambda_{540}$ image. Specifically, the enhanced image creator 120 extracts, as information to be enhanced, information that is represented remarkably in the $\lambda_{415}$ image as a result of calculation of each of differences of the $\lambda_{415}$ from the $\lambda_{460}$ image and the $\lambda_{630}$ image, regards the obtained information as an amount of enhancement and synthesizes the amount of enhancement and the $\lambda_{540}$ image. The amount of enhancement is, for example, the average of the difference between the $\lambda_{460}$ image and the $\lambda_{415}$ image and the difference between the $\lambda_{630}$ image and the $\lambda_{415}$ image or the larger or smaller one of the two differences. The enhancing method is not limited to this process, and any other method may be used as long as the method is a process to enhance a specific image based on multiple images. Alternatively, a process to enhance a subject to be enhanced by reducing the contrast of parts other than the part to be enhanced may be used. When it is determined that the $\lambda_{540}$ image is not updated, the enhanced image creator 120 acquires the $\lambda_{540}$ image that is the enhanced image previously created and regards this $\lambda_{540}$ image as the enhanced image in the latest frame.

Figure 2:
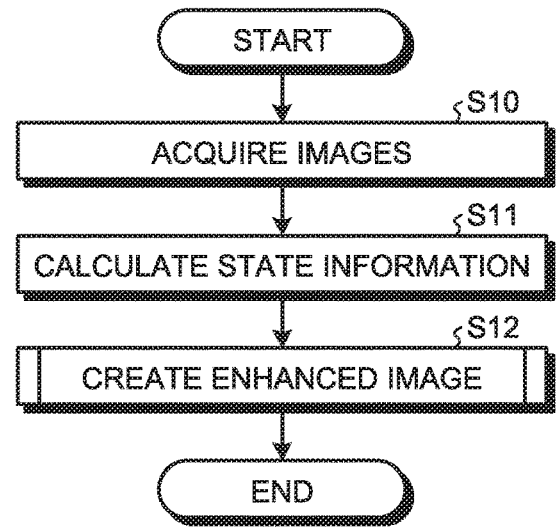
FIG. 2 is a flowchart illustrating image processing that is performed by the image processing device according to the first embodiment.

Operations of the image processing device 1 will be described. FIG. 2 is a flowchart illustrating the image processing performed by the image processing device 1. First of all, at step S10, the image acquisition unit 20 acquires multiple images corresponding to center wavelengths that are different from one another. Specifically, the image acquisition unit 20 sequentially acquires a $\lambda_{415}$ image, a $\lambda_{460}$ image, a $\lambda_{540}$ image and a $\lambda_{630}$ image that are four narrowband images that are acquired respectively using the four narrowband lights whose center wavelengths are 415 nm, 460 nm, 540 nm and 630 nm.

As an exemplary method of acquiring narrowband images with an endoscope, a method using LEDs that emit light with wavelength peaks of multiple narrowbands is taken. For example, four light emitting diodes (LEDs) that emit four narrowband lights whose center wavelengths are 415 nm, 460 nm, 540 nm and 630 nm, respectively, are provided and the LEDs are sequentially caused to emit light to illuminate the inside of the living body and each of the lights reflected from the inside of the living body is acquired by a color imaging device according to each narrowband light. Accordingly, four narrowband images respectively corresponding to center wavelengths of 415 nm, 460 nm, 540 nm and 630 nm can be acquired. The actual center wavelengths of the narrowband lights applied to acquire the narrowband images may be values around the aforementioned 415 nm, 460 nm, 540 nm and 630 nm.

At the following step S11, the state information calculator 110 calculates state information on the $\lambda_{540}$ image. Specifically, the update determination unit 111a determines whether the $\lambda_{540}$ image is the narrowband image in the latest frame. The chronological information calculator 111 calculates chronological information on the $\lambda_{540}$ image based on a result of determination performed by the update determination unit 111a. The state information calculator 110 outputs the chronological information on the $\lambda_{540}$ image, which is calculated by the chronological information calculator 111, as state information to the enhanced image creator 120.

Figure 3:
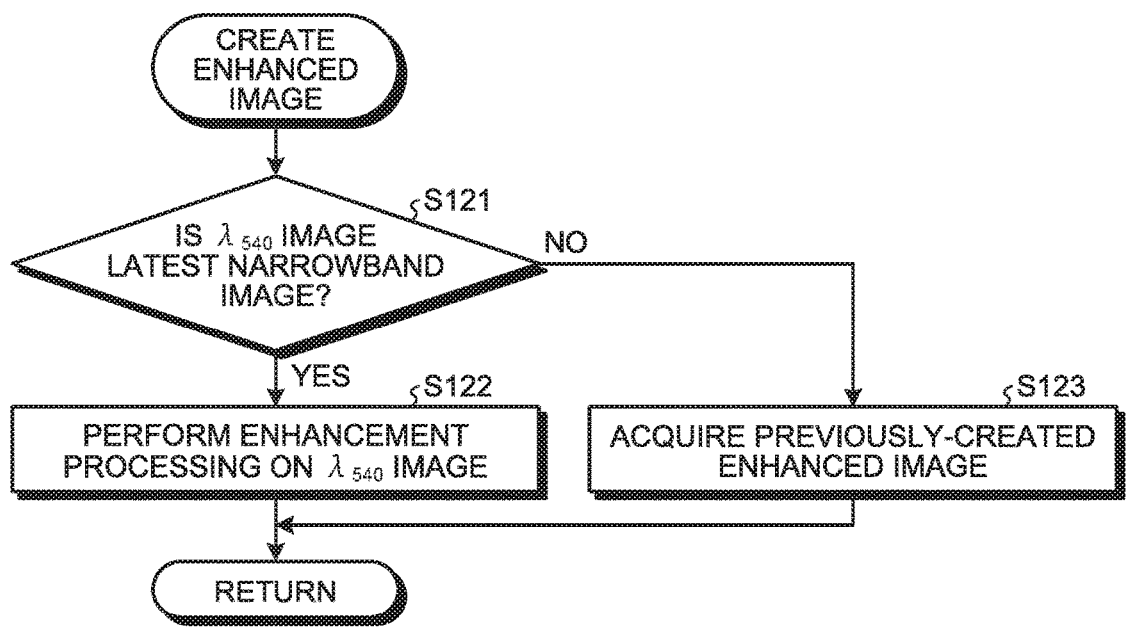
FIG. 3 is a flowchart illustrating a process of creating an enhanced image according to the first embodiment.

At the following step S12, the enhanced image creator 120 creates an enhanced image of the $\lambda_{540}$ image. FIG. 3 is a flowchart representing the process of creating an enhanced image according to the first embodiment.

At step S121, the enhanced image creator 120 determines whether the $\lambda_{540}$ image that is the narrowband image to be enhanced is a frame that is updated in the latest frame based on the state information that is calculated by the state information calculator 110.

When it is determined that the enhanced image creator 120 is the narrowband image in the latest frame (YES at step S121), the enhanced image creator 120 performs enhancement processing on the $\lambda_{540}$ image (step S122). A described above, the enhanced image creator 120 synthesizes the $\lambda_{540}$ image and an amount of enhancement based on each of the differences of the $\lambda_{415}$ image from the $\lambda_{460}$ image and the $\lambda_{630}$ image. The enhanced image creator 120 regards the synthesized $\lambda_{540}$ image as the enhanced image. The controller 10 then returns to the main routine and ends the image processing. The controller 10 further preforms control to cause the display unit 40 to display the $\lambda_{540}$ image on which the enhancement processing is performed.

On the other hand, when it is determined that the $\lambda_{540}$ image is not the narrowband image in the latest frame (NO at step S121), the enhanced image creator 120 acquires the $\lambda_{540}$ image that is the enhanced image previously created and regards the acquired $\lambda_{540}$ image as the enhanced image in the latest frame (step S123).

Figure 4:
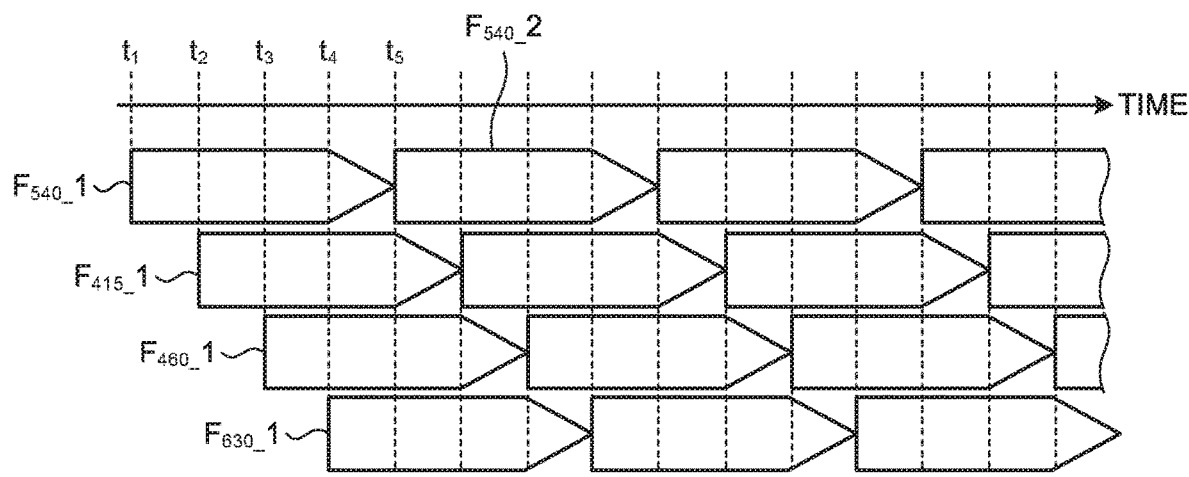
FIG. 4 is a diagram illustrating images that are acquired in the image processing that is performed by the image processing device according to the first embodiment.

Steps S122 and S123 enable creation of an enhanced image corresponding to the context of update of the $\lambda_{540}$ image. FIG. 4 is a diagram illustrating the images that are acquired in the image processing performed by the image processing device according to the first embodiment. As described above, the image acquisition unit 20 sequentially acquires four narrowband images that are captured respectively using the four narrowband lights whose center wavelengths are 415 nm, 460 nm, 540 nm and 630 nm. As illustrated in FIG. 4, when the narrowband lights of 540 nm, 415 nm, 460 nm and 630 nm are emitted according to the order they appear in this sentence and the $\lambda_{540}$ image, the $\lambda_{415}$ image, the $\lambda_{460}$ image and the $\lambda_{630}$ image corresponding to the narrowband lights are acquired sequentially, for example, a frame $F_{540\_1}$ that is the $\lambda_{540}$ image is acquired at Time $t_1$, a frame $F_{415\_1}$ that is the $\lambda_{415}$ image is acquired at Time $t_2$, a frame $F_{460\_1}$ that is the $\lambda_{460}$ image is acquired at Time $t_3$, and a frame $F_{630\_1}$ that is the $\lambda_{630}$ image is acquired at Time $t_4$. Thereafter, a frame $F_{540\_2}$ that is the $\lambda_{540}$ image is acquired again at Time $t_5$ and acquisition of the frames of the $\lambda_{540}$ image, the $\lambda_{415}$ image, the $\lambda_{460}$ image and the $\lambda_{630}$ image is repeated in the aforementioned order.

As in the case illustrated in FIG. 4, the update determination unit 111a determines that the $\lambda_{540}$ image that is the narrowband image to be enhanced is the narrowband image in the latest frame at Times $t_1$ and $t_5$. The enhanced image creator 120 executes the enhancement processing on the $\lambda_{540}$ image at Times $t_1$ and $t_5$.

On the other hand, the update determination unit 111a determines that the $\lambda_{540}$ image that is the narrowband image to be enhanced is not the narrowband image in the latest frame at Times $t_2$ to $t_4$. In this case, the enhanced image creator 120 regards the $\lambda_{540}$ image on which the enhancement processing is performed previously as the enhanced image at Times $t_2$ to $t_4$. Specifically, the enhanced image creator 120 regards the $\lambda_{540}$ image on which the enhancement processing is performed at Time $t_1$ as the enhanced image at Times $t_2$ to $t_4$.

According to the first embodiment described above, the enhanced image creator 120 performs the enhancement processing on the $\lambda_{540}$ image according to the context of update of the $\lambda_{540}$ image that is the narrowband image to be enhanced, thereby enabling generation of an appropriate enhanced image according to the acquired images.

According to the first embodiment, the enhanced image creator 120 executes any one of performing the enhancement processing on the $\lambda_{540}$ image and regarding the $\lambda_{540}$ image on which the enhancement processing is performed previously as the current enhanced image according to the context of update of the $\lambda_{540}$ image that is the narrowband image to be enhanced, thereby enabling inhibition of the enhanced image from blurring when the enhancement processing is performed on the image that is displayed in chronological order.

The wavelength band of light to be applied and the order of application of light and the imaging unit are not limited to the above-described first embodiment, and images not used for enhancement may be captured. For example, simultaneous emission of narrowband lights whose center wavelengths are 415 nm, 540 nm and 630 nm and simultaneous emission of narrowband lights whose center wavelengths are 460 nm, 540 nm and 600 nm may be repeated alternately to acquire narrowband images captured by a Bayer sensor or a three CCD sensor. The light source to be used is not limited, and LEDs, a Xenon light source or a laser light source may be used.

As another exemplary method of acquiring narrowband images, a method in which a narrowband filter is arranged in front of a white light source, such as a Xenon lamp, and the inside of a living body is irradiated sequentially with light whose bandwidth is narrowed by the narrowband filter or a method of sequentially driving multiple laser diodes that respectively emit lights whose center wavelengths are different from one another can be exemplified. Furthermore, the inside of the living body may be irradiated with white light and the reflected light from the living body may be caused to be incident on the imaging device via a narrowband filter to acquire a narrowband image.

Modification 1 of First Embodiment

Figure 5:
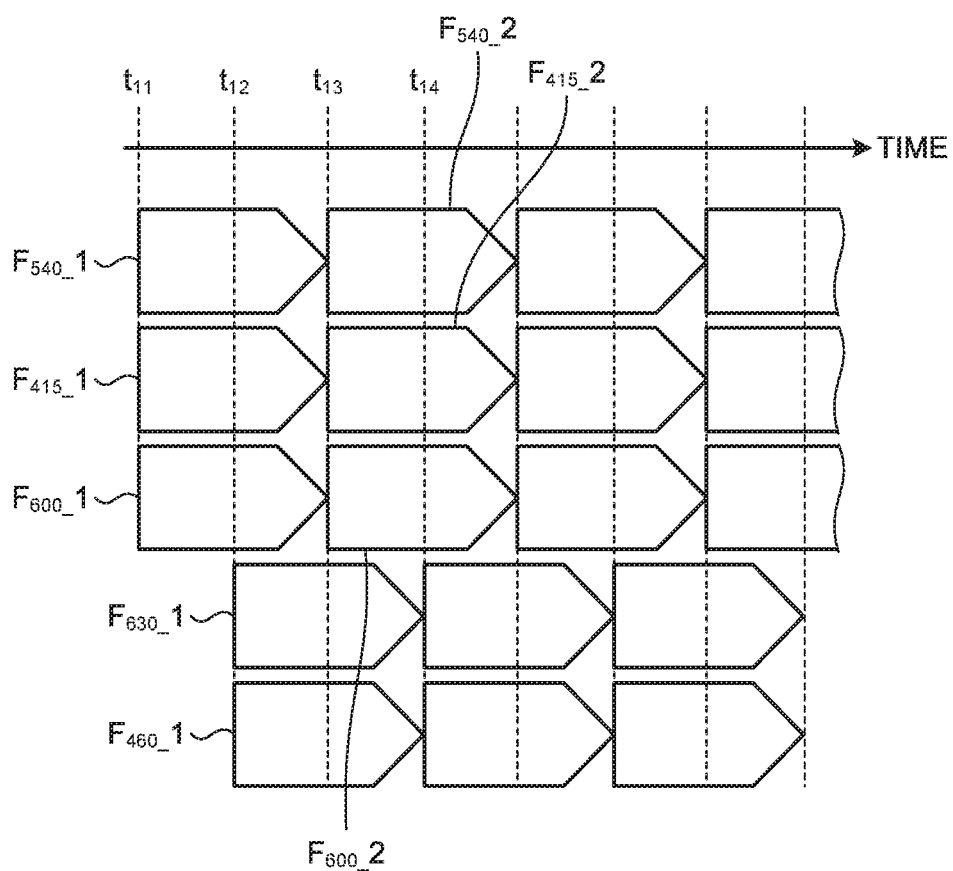
FIG. 5 is a diagram illustrating an image that is acquired in image processing that is performed by an image processing device according to Modification 1 of the first embodiment.

Modification 1 of the first embodiment will be described. FIG. 5 is a diagram illustrating images that are acquired in image processing performed by the image processing device according to Modification 1 of the first embodiment. The above-described first embodiment has been described as one where four narrowband lights whose center wavelengths are 415 nm, 460 nm, 540 nm and 630 nm are emitted sequentially to acquire a $\lambda_{415}$ image, a $\lambda_{460}$ image, a a $\lambda_{540}$ image and a $\lambda_{630}$ image. In Modification 1, simultaneous emission of narrowband lights whose center wavelengths are respectively 415 nm, 540 nm and 600 nm and simultaneous emission of narrowband lights whose center wavelengths are respectively 460 nm and 630 nm are repeated alternately to acquire narrowband images.

In Modification 1, observation light containing multiple narrowband lights having center wavelengths, respectively, is dispersed with a dispersive member, such as a prism, to acquire narrowband images corresponding to the respective narrowband lights. In this case, as illustrated in FIG. 5, at Time $t_{11}$, a frame $F_{540\_1}$ that is a $\lambda_{540}$ image, a frame $F_{415\_1}$ that is a $\lambda_{415}$ image and a frame $F_{600\_1}$ that is a $\lambda_{600}$ image are acquired and, at Time $t_{12}$, a frame $F_{460\_1}$ that is a $\lambda_{460}$ image and a frame $F_{630\_1}$ that is a $\lambda_{630}$ image are acquired. Thereafter, at Time $t_{13}$, a frame $F_{540\_2}$ that is a $\lambda_{540}$ image, a frame $F_{415\_2}$ that is a $\lambda_{415}$ image and a frame $F_{600\_2}$ that is a $\lambda_{600}$ image are acquired again and, at Time $t_{14}$, a $\lambda_{460}$ image and a $\lambda_{630}$ image are acquired. As described above, in Modification 1, in the time to acquire narrowband images of two frames, acquisition of a $\lambda_{415}$ image, a $\lambda_{460}$ image, a $\lambda_{540}$ image, a $\lambda_{600}$ image and a $\lambda_{630}$ image can be performed repeatedly. In Modification 1, when the process is performed according to the flowchart of the above-described first embodiment, the $\lambda_{415}$ image, the $\lambda_{460}$ image, the $\lambda_{540}$ image and the $\lambda_{630}$ image are narrowband images used for enhancement and the $\lambda_{600}$ image is a narrowband image that is not used for enhancement.

In Modification 1, the update determination unit 111a determines that the $\lambda_{540}$ image that is a narrowband image to be enhanced is the narrowband image in the latest frame at Times $t_{11}$ and $t_{13}$. The enhanced image creator 120 executes the enhancement processing on the $\lambda_{540}$ image at the times $t_{11}$ and $t_{13}$.

On the other hand, the update determination unit 111a determines that the $\lambda_{540}$ image that is the narrowband image to be enhanced is not the narrowband image in the latest frame at Times $t_{12}$ and $t_{14}$. In this case, the enhanced image creator 120 regards the $\lambda_{540}$ image on which the enhancement processing is performed previously as an enhanced image at times $t_{12}$ and $t_{14}$. Specifically, at $t_{12}$, the enhanced image creator 120 regards the $\lambda_{540}$ image on which the enhancement processing is performed at Time $t_1$ as an enhanced image and, at time $t_{14}$, regards the $\lambda_{540}$ image on which the enhancement processing is performed at $t_{13}$ as an enhanced image. As described above, in Modification 1, the $\lambda_{540}$ image on which the enhancement processing is performed in the frame on which the determination is made currently and the $\lambda_{540}$ image on which the enhancement processing is performed previously are selected alternately as enhanced images.

According to Modification 1 described above, as simultaneous emission of light containing multiple narrowband lights having center wavelengths, respectively, enables acquisition of narrowband images by the multiple narrowband lights different from one another, it is possible to inhibit an enhanced image from blurring when an image that is displayed in chronological order is displayed in an enhanced manner and increase the frequency at which the enhancement processing is performed on the $\lambda_{540}$ image.

Modification 2 of First Embodiment

Figure 6:
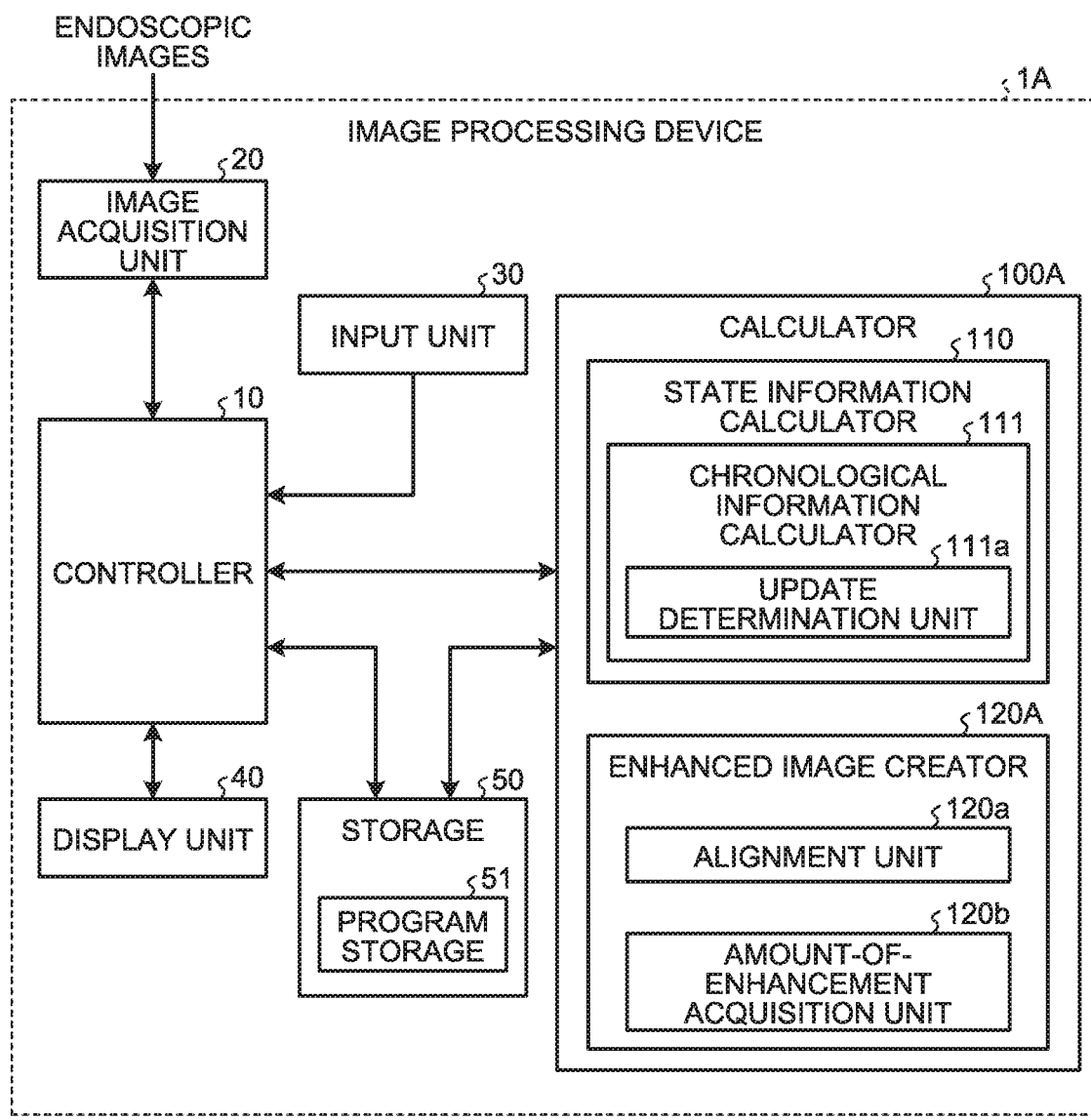
FIG. 6 is a block diagram illustrating a functional configuration of an image processing device according to Modification 2 of the first embodiment.

Modification 2 of the first embodiment will be described. FIG. 6 is a block diagram illustrating a functional configuration of an image processing device according to Modification 2 of the first embodiment. An image processing device 1A according to Modification 2 includes a calculator 100A instead of the calculator 100 represented in FIG. 1. The calculator 100A includes an enhanced image creator 120A instead of the enhanced image creator 120 represented in FIG. 1. Note that the configuration and operations of each of the components of the calculator excluding the enhanced image creator 120A and the configuration and operations of each of the components of the image processing device excluding the calculator are the same as those of the first embodiment.

Based on the state information that is calculated by the state information calculator 110, the enhanced image creator 120A synthesizes a $\lambda_{540}$ image and information that is extracted based on a $\lambda_{415}$ image, a $\lambda_{460}$ image and a $\lambda_{630}$ image, thereby performing the enhancement processing on the $\lambda_{540}$ image. The enhanced image creator 120A includes an alignment unit 120a and an amount-of-enhancement acquisition unit 120b.

The alignment unit 120a performs alignment between the latest $\lambda_{540}$ image and the $\lambda_{540}$ image (also referred to as old $\lambda_{540}$ image) in the frame before the latest $\lambda_{540}$ image. The alignment unit 120a performs alignment by a known method, such as pattern matching using any one of the images as a template. The old $\lambda_{540}$ image may be the frame one frame before or a frame dating back by a number of times that is set.

Based on the result of the alignment performed by the alignment unit 120a, the amount-of-enhancement acquisition unit 120b acquires an amount of enhancement that is set for the old $\lambda_{540}$ image according to the position of the latest $\lambda_{540}$ image.

In Modification 2, the update determination unit 111a determines whether the $\lambda_{540}$ image that is a narrowband image to be enhanced is the narrowband image in the latest frame and determines whether the $\lambda_{415}$ image in which information to be enhanced is represented in high contrast is the narrowband image in the latest frame. In other words, the $\lambda_{415}$ image is a narrowband image in which the amount of information to be enhanced, for example, contrast information on blood-vessel components required to be enhanced is large relatively to other narrowband images.

Operations of the image processing device 1A will be described. The image processing device 1A performs processing according to the same flow as steps S10 to S12 illustrated in FIG. 2. First of all, the image acquisition unit 20 sequentially acquires a $\lambda_{415}$ image, a $\lambda_{460}$ image, a $\lambda_{540}$ image and a $\lambda_{630}$ image.

Thereafter, in the image processing device 1A, the state information calculator 110 calculates state information on the $\lambda_{540}$ image and the $\lambda_{415}$ image.

Figure 7:
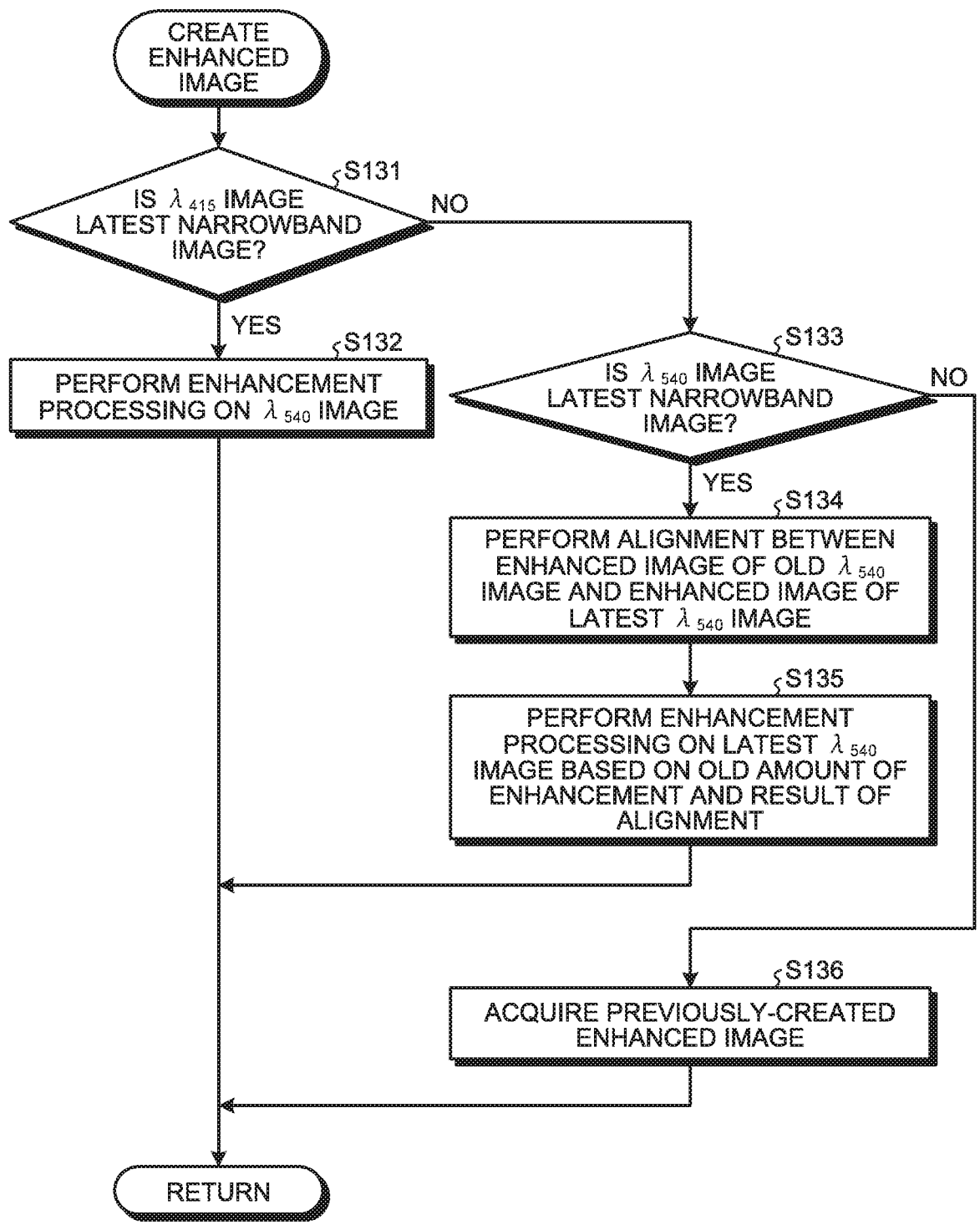
FIG. 7 is a flowchart illustrating a process of creating an enhanced image in Modification 2 of the first embodiment.

Subsequently, the enhanced image creator 120A creates an enhanced image of the $\lambda_{540}$ image. FIG. 7 is a flowchart illustrating a process of creating an enhanced image in Modification 2 of the first embodiment.

At step S131, based on the state information that is calculated by the state information calculator 110, the enhanced image creator 120A determines whether the $\lambda_{415}$ image is the narrowband image in the latest frame.

When it is determined that the $\lambda_{415}$ image is the narrowband image in the latest frame (YES at step S131), the enhanced image creator 120A performs the enhancement processing on the $\lambda_{540}$ image (step S132). As described above, the enhanced image creator 120A synthesizes the $\lambda_{540}$ image and an amount of enhancement based on each of the differences of the $\lambda_{415}$ image from the $\lambda_{460}$ image and the $\lambda_{630}$ image. The enhanced image creator 120A regards the synthesized $\lambda_{540}$ image as the enhanced image. The controller 10 then returns to the main routine and ends the image processing. The controller 10 further preforms control to cause the display unit 40 to display the $\lambda_{540}$ image on which the enhancement processing is performed.

On the other hand, when it is determined that the $\lambda_{415}$ image is not the narrowband image in the latest frame (NO at step S131), the enhanced image creator 120A moves to step S133.

At step S133, based on the state information that is calculated by the state information calculator 110, the enhanced image creator 120A determines whether the $\lambda_{540}$ image that is the narrowband image to be enhanced is the narrowband image in the latest frame.

When it is determined that the $\lambda_{540}$ image is the narrowband image in the latest frame (YES at step S133), the enhanced image creator 120A moves to step S134.

At step S134, the alignment unit 120a performs alignment between the $\lambda_{540}$ image of the latest frame and the old the $\lambda_{540}$ image.

At step S135 following step S134, based on the result of alignment performed by the alignment unit 120a, the enhanced image creator 120A executes the enhancement processing on the $\lambda_{540}$ image of the latest frame. Specifically, based on the result of alignment performed by the alignment unit 120a, the amount-of-enhancement acquisition unit 120b acquires the amount of enhancement that is set for the old $\lambda_{540}$ image according to the position of the latest $\lambda_{540}$ image. The enhanced image creator 120A executes the enhancement processing on the $\lambda_{540}$ image of the latest frame based on the amount of enhancement that is acquired by the amount-of-enhancement acquisition unit 120b. The controller 10 then returns to the main routine and ends the image processing. The controller 10 further performs control to cause the display unit 40 to display the $\lambda_{540}$ image on which the enhancement processing is performed.

On the other hand, when it is determined that the $\lambda_{540}$ image is not the narrowband image in the latest frame (NO at step S133), the enhanced image creator 120A acquires the $\lambda_{540}$ image that is the enhanced image that is created previously and regards the acquired $\lambda_{540}$ image as the enhanced image in the latest frame (step S136). Thereafter, the controller 10 returns to the main routine and ends the image processing. The controller 10 further performs control to cause the display unit 40 to display the $\lambda_{540}$ image on which the enhancement processing is performed.

In Modification 2, the above-described steps S132, S135 and 5136 enables creation of an enhanced image corresponding to the context of update of the $\lambda_{540}$ image and the $\lambda_{415}$ image.

According to Modification 2 described above, according to the context of update between the $\lambda_{540}$ image that is the narrowband image to be enhanced and the $\lambda_{415}$ image with a large volume of information that should be enhanced, the enhanced image creator 120A executes any one of performing the enhancement processing on the $\lambda_{540}$ image and causing the current enhanced image to reflect the information on the $\lambda_{540}$ image on which the enhancement processing is performed previously, thereby enabling generation of an appropriate enhanced image according to the acquired image and inhibition of the enhanced image from blurring when the enhancement processing is performed on the image that is displayed in chronological order.

In modification 2, the narrowband mage in which information to be enhanced is represented in high contrast is set previously and, for example, is set as the $\lambda_{415}$ image. The narrowband image to be set is not is not limited to one image and, for example, two narrowband images like the $\lambda_{415}$ image and the $\lambda_{460}$ image may be set.

In Modification 2, the method of enhancing the latest the $\lambda_{540}$ image using the old amount of enhancement when the $\lambda_{540}$ image is updated is exemplified. Alternatively, when the $\lambda_{540}$ image is updated, the enhanced image previously created may serve as the enhanced image in the latest frame.

Second Embodiment

Figure 8:
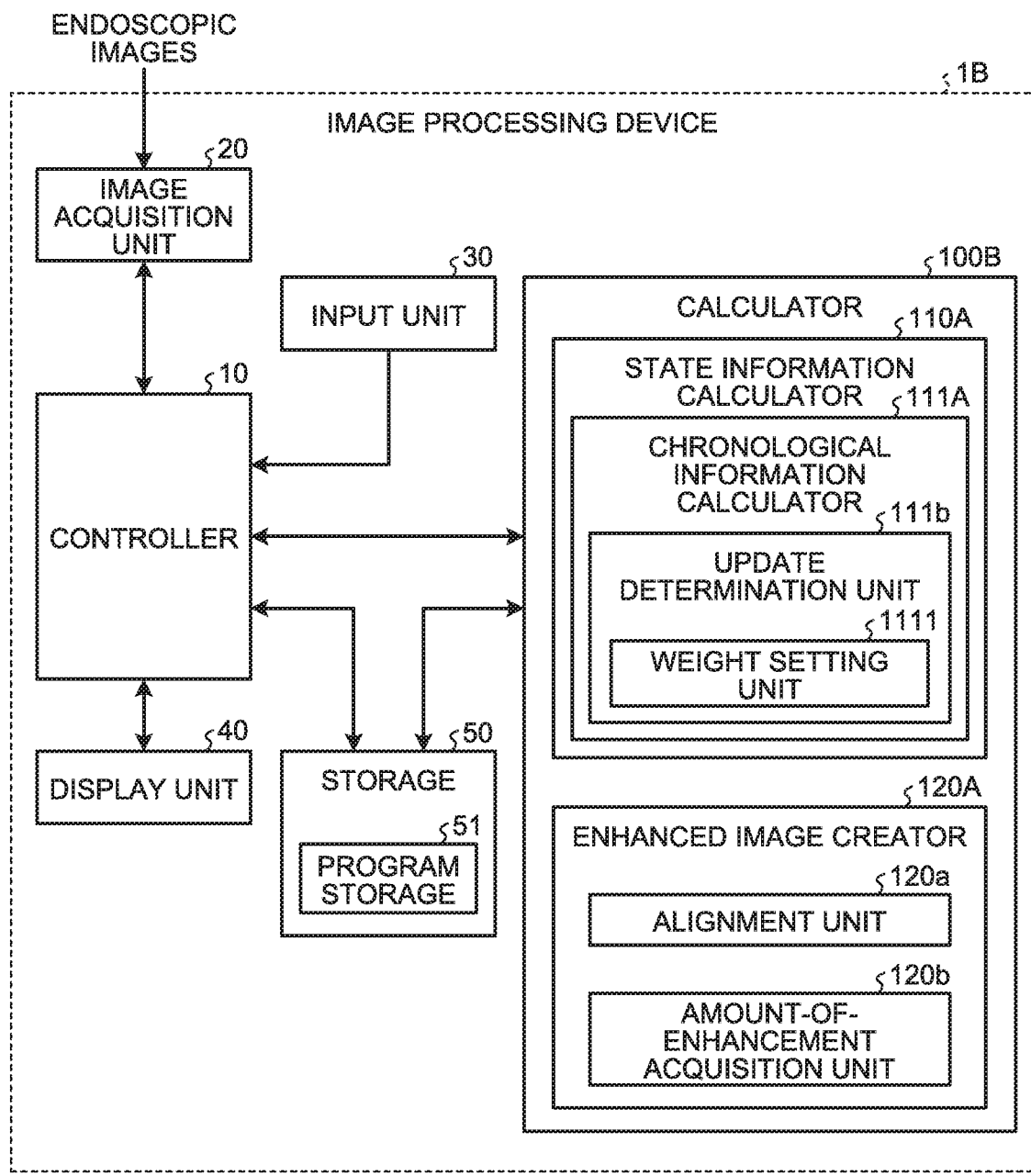
FIG. 8 is a block diagram illustrating a functional configuration of an image processing device according to a second embodiment.

A second embodiment will be described. FIG. 8 is a block diagram illustrating a functional configuration of an image processing device according to a second embodiment. As illustrated in FIG. 8, an image processing device 1B according to a second embodiment includes a calculator 100B instead of the calculator 100A represented in FIG. 6. The calculator 100B includes a state information calculator 110A instead of the state information calculator 110 illustrated in FIG. 6. Note that the configuration and operations of each of the components of the calculator excluding the state information calculator 110A and the configuration and operations of each of the components of the image processing device excluding the calculator are the same as those of Example 2 of the first embodiment.

The state information calculator 110A includes a chronological information calculator 111A that calculates chronological information on a narrowband image. The chronological information calculator 111A includes an update determination unit 111b that determines an update state of a narrowband image to be used for enhancement.

The update determination unit 111b determines whether the narrowband image in the latest frame is any one of a $\lambda_{415}$ image, a $\lambda_{460}$ image, a $\lambda_{540}$ image and a $\lambda_{630}$ image described above.

The update determination unit 111b includes a weight setting unit 1111 that sets weights used for enhancement processing. The weights that are set by the weight setting unit 1111 are values that are set for respective narrowband images based on the amount of information to be enhanced. The weights are set such that a larger weight is set for a narrowband image with information to be enhanced in higher contrast. Specifically, when blood vessels represented markedly in the $\lambda_{415}$ image are extracted as information to be enhanced, the weight in the $\lambda_{415}$ image with the blood vessels in high contrast is the largest. In the second embodiment, the weight setting unit 1111 acquires a value that is set in advance. The weight according to the second embodiment functions as a determination value for determining whether to perform the enhancement processing.

From the result of determination made by the update determination unit 111b, the state information calculator 110A determines which one of a $\lambda_{415}$ image, a $\lambda_{460}$, a $\lambda_{540}$ image and a $\lambda_{630}$ image the narrowband image in the latest frame is from the result of the determination made by the update determination unit 111b. Thereafter, the weight setting unit 1111 sets a weight for the narrowband image that is updated in the latest frame and the state information calculator 110A calculates the set weight as state information. Note that, when multiple narrowband images are acquired at a time with the above-described simultaneous lights, the weights that are set for the respective narrowband images are summed and the sum serves as the state information.

Figure 9:
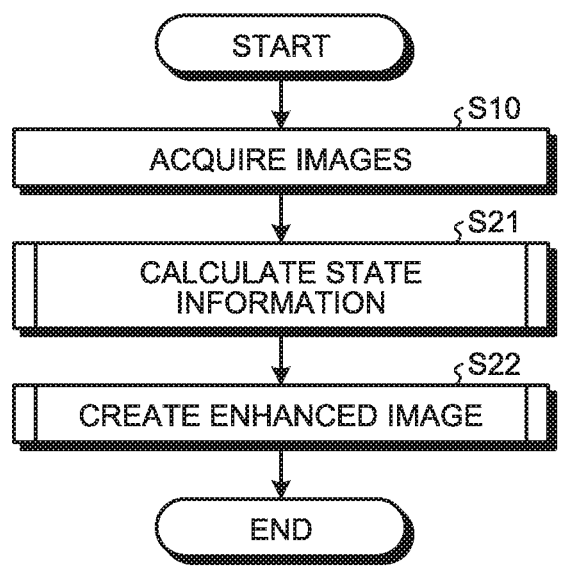
FIG. 9 is a flowchart illustrating image processing that is performed by the image processing device according to the second embodiment.

Operations of the image processing device 1B will be described. FIG. 9 is a flowchart illustrating image processing performed by the image processing device 1B. First of all, at step S10, the image acquisition unit 20 sequentially acquires a $\lambda_{415}$ image, a $\lambda_{460}$ image, a $\lambda_{540}$ image and a $\lambda_{630}$ image that are four narrowband images acquired respectively using four narrowband lights whose center wavelengths are 415 nm, 460 nm, 540 nm and 630 nm.

Figure 10:
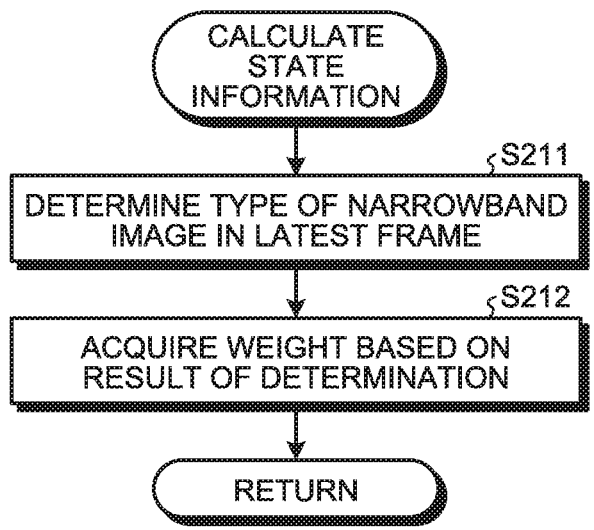
FIG. 10 is a flowchart illustrating a process of calculating state information in the second embodiment.

At the following step S21, the state information calculator 110A calculates state information on a narrowband image. FIG. 10 is a flowchart illustrating a process of calculating state information in the second embodiment.

At step S211, the update determination unit 111b determines a type of the narrowband image in the latest frame. Specifically, the update determination unit 111b determines which one of the $\lambda_{415}$ image, the $\lambda_{460}$ image, the $\lambda_{540}$ image and the $\lambda_{630}$ image the narrowband image in the latest frame is.

At step S212 following step S211, based on the determination made by the update determination unit 111b, the weight setting unit 1111 acquires a weight corresponding to the updated narrowband image. The state information calculator 110A acquires a weight of the narrowband image that is updated in the latest frame and sets the acquired weight as state information.

Figure 11:
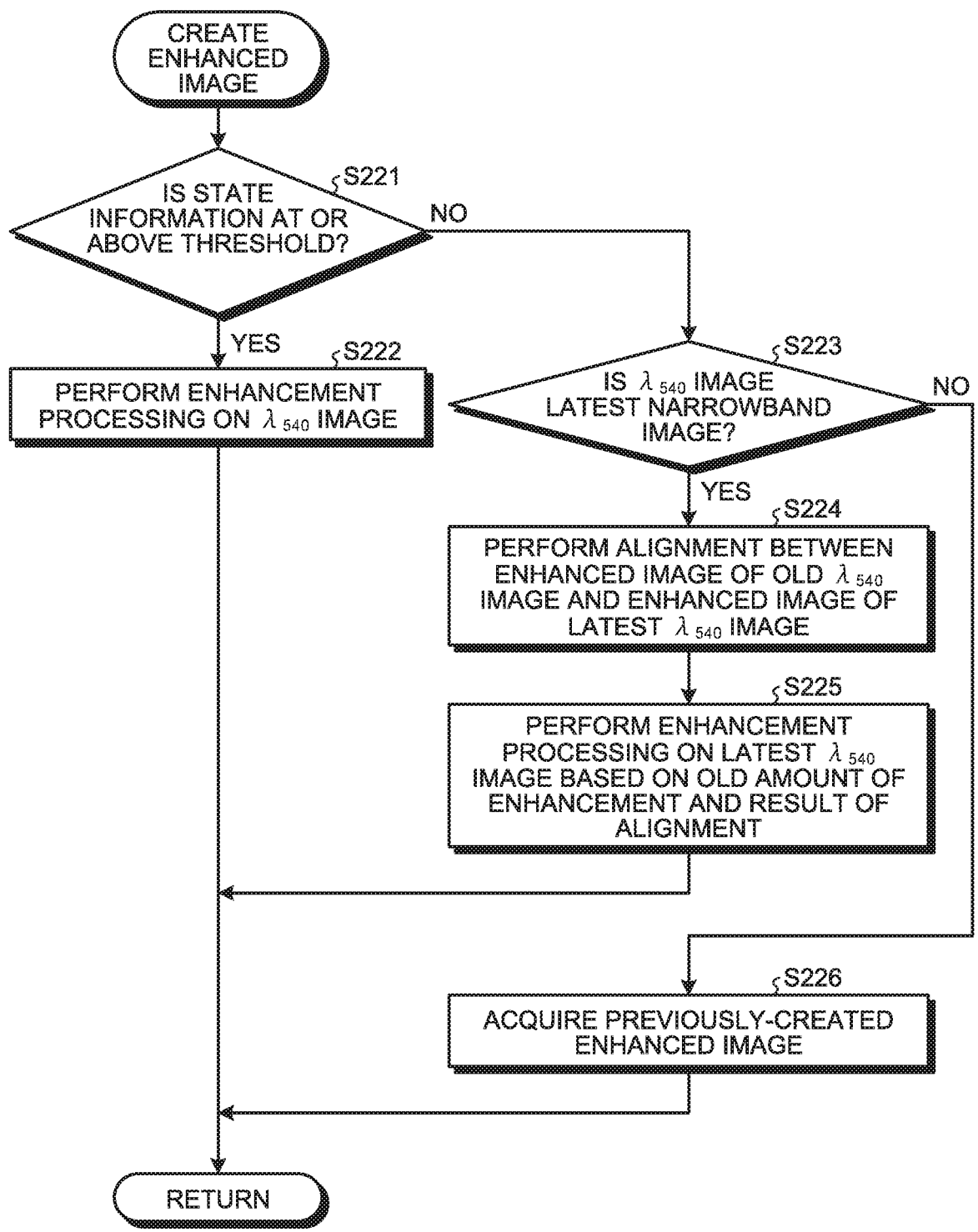
FIG. 11 is a flowchart illustrating a process of creating an enhanced image in the second embodiment.

At the following step S22, the enhanced image creator 120A creates an enhanced image of the $\lambda_{540}$ image. FIG. 11 is a flowchart illustrating the process of creating an enhanced image in the second embodiment.

At step S221, the enhanced image creator 120A determines whether the state information that is calculated by the state information calculator 110A is at or above a threshold. Specifically, the enhanced image creator 120A determines whether the weight that is set as the state information is at or above the pre-set threshold. As the threshold, for example, a value corresponding to the largest weight is set.

When the enhanced image creator 120A determines that the weight is at or above the threshold (YES at step S221), the enhanced image creator 120A performs enhancement processing on the $\lambda_{540}$ image (step S222). As described above, the enhanced image creator 120A synthesizes the $\lambda_{540}$ image and the enhancement amount based on differences of the $\lambda_{415}$ image from the $\lambda_{460}$ image and the $\lambda_{630}$ image. The enhanced image creator 120A regards the synthesized $\lambda_{540}$ image as an enhanced image. Thereafter, the controller 10 returns to the main routine and ends the image processing. The controller 10 then performs control to cause the display unit 40 to display the $\lambda_{540}$ image on which the enhancement processing is performed.

On the other hand, when it is determined that the weight is under the threshold (NO at step S221), the enhanced image creator 120 moves to step S223.

At step S223, based on the state information that is calculated by the state information calculator 110A, the enhanced image creator 120A determines whether the $\lambda_{540}$ image that is a narrowband image to be enhanced is the narrowband image in the latest frame.

When it is determined that the $\lambda_{540}$ image is the narrowband image in the latest frame (YES at step S223), the enhanced image creator 120A moves to step S224.

At step S224, the alignment unit 120a performs alignment between the $\lambda_{540}$ image of the latest frame and the old $\lambda_{540}$ image.

At step S225 following step S224, based on the result of alignment performed by the alignment unit 120a, the enhanced image creator 120A executes the enhancement processing on the latest $\lambda_{540}$ image. Specifically, based on the result of alignment performed by the alignment unit 120a, the amount-of-enhancement acquisition unit 120b acquires the amount of enhancement that is set for the old $\lambda_{540}$ image according to the position of the latest $\lambda_{540}$ image. Based on the amount of enhancement that is acquired by the amount-of-enhancement acquisition unit 120b, the enhanced image creator 120A executes the enhancement processing on the $\lambda_{540}$ image of the latest frame. Thereafter, the controller 10 returns to the main routine and ends the image processing. The controller 10 performs control to cause the display unit 40 to display the $\lambda_{540}$ image on which the enhancement processing is performed.

On the other hand, when it is determined that the $\lambda_{540}$ image is not the narrowband image in the latest frame (NO at step S223), the enhanced image creator 120A acquires the $\lambda_{540}$ image that is the previously-created enhanced image and uses the $\lambda_{540}$ image as the enhanced image in the latest frame (step S226). Thereafter, the controller 10 returns to the main routine and ends the image processing. The controller 10 then performs control to cause the display unit 40 to display the $\lambda_{540}$ image on which the enhancement processing is performed.

In the second embodiment, the above-described steps S222, S225 and S226 create an enhanced image corresponding to the context of update of the narrowband image.

According to the second embodiment described above, according to the context of update of the weighted narrowband image, the enhanced image creator 120A executes any one of performing the enhancement processing on the $\lambda_{540}$ image and causing the current enhanced image to reflect the information on the $\lambda_{540}$ image on which the enhancement processing is performed previously, thereby enabling generation of an appropriate enhanced image according to the acquired image and inhibition of the enhanced image from blurring when the enhancement processing is performed on the image that is displayed in chronological order.

In the above-described second embodiment, a weight is set based on the contrast of the information to be enhanced. Alternatively, a weight may be set such that the weight of the image to be enhanced is larger than the weights of other images.

Modification 1 of Second Embodiment

Modification 1 of the second embodiment will be described. The above-described second embodiment has been described as one where a pre-set weight is used. In Modification 1, a weight is set adaptively according to a mode of observation and a condition that is input and set.

Figure 12:
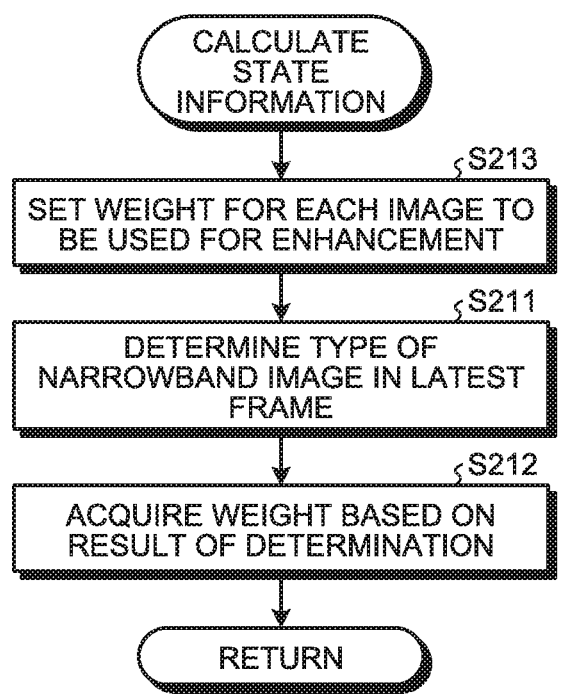
FIG. 12 is a flowchart illustrating a process of calculating state information in Modification 1 of the second embodiment.

FIG. 12 is a flowchart illustrating a process of calculating state information in Modification 1 of the second embodiment. At step S213, based on the result of determination made by the weight setting unit 1111, the weight setting unit 1111 sets weights corresponding to the updated narrowband image. The weight setting unit 1111 sets weights for respective narrowband images according to the mode of observation and the condition that is input and set. For example, the weight setting unit 1111 sets weights such that the weight for a narrowband image with information of blood vessels to be observed in high contrast is large in, for example, a mode to observe blood vessels on the surface layer or a mode to observe blood vessels in a deep part.

At step S211 following step S213, the update determination unit 111b determines which one of the $\lambda_{415}$ image, the $\lambda_{460}$ image, the $\lambda_{540}$ image and the $\lambda_{630}$ image the narrowband image in the latest frame is.

At step S212 following step S211, based on the result of the determination made by the update determination unit 111b, the weight setting unit 1111 acquires a weight corresponding to the narrowband image in the latest frame. The state information calculator 110A acquires a weight for the narrowband image in the latest frame and sets the acquired weight as state information.

As described above, a weight may be set adaptively according to a subject to be observed and the setting in the enhancement processing may be changed according to the mode that is properly set during observation.

Modification 2 of Second Embodiment

Figure 13:
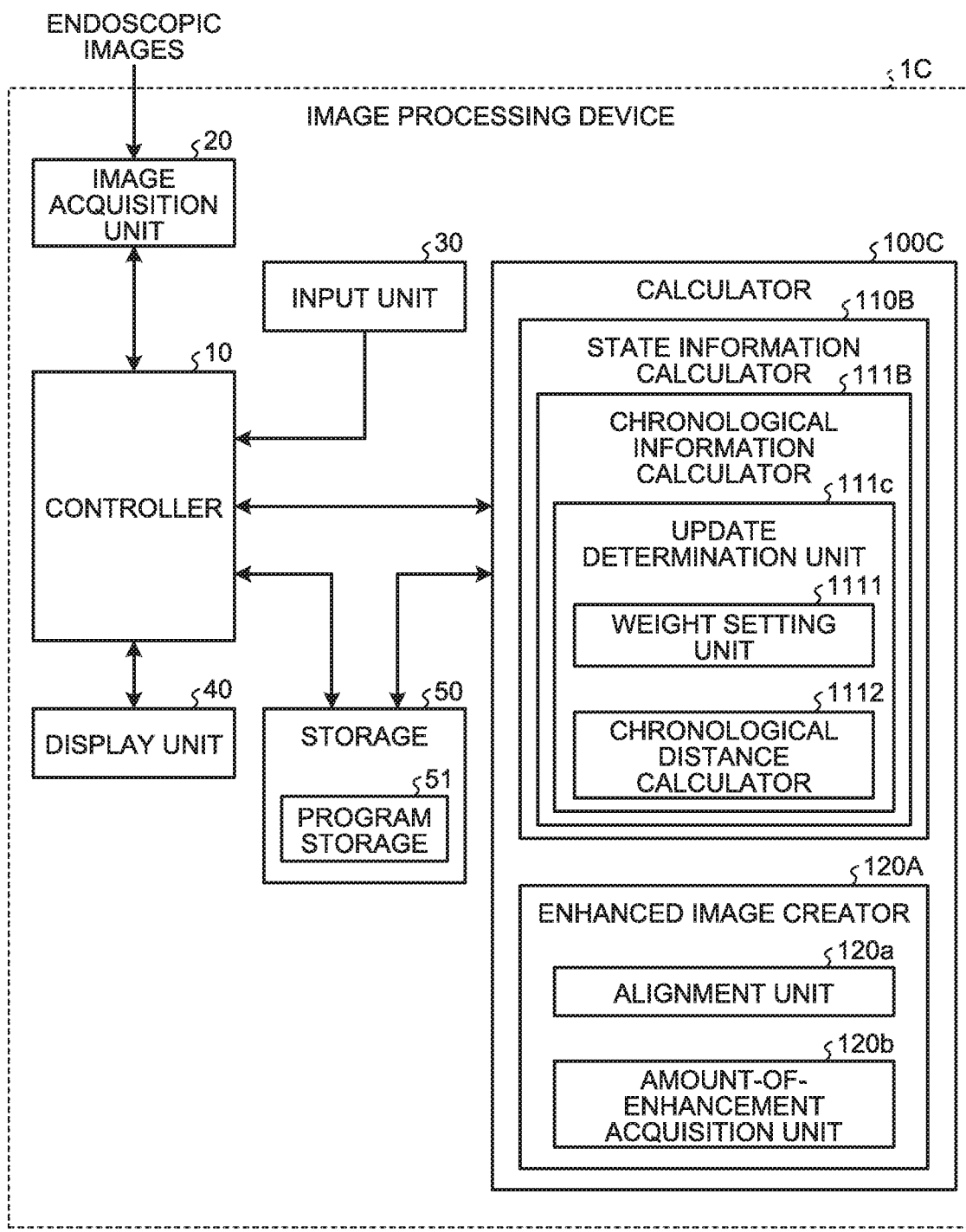
FIG. 13 is a block diagram illustrating a functional configuration of an image processing device according to Modification 2 of the second embodiment.

Modification 2 of the second embodiment will be described. FIG. 13 is a block diagram illustrating a functional configuration of an image processing device according to Modification 2 of the second embodiment. An image processing device 1C according to Modification 2 includes a calculator 100C instead of the calculator 100B represented in FIG. 8. The calculator 100C includes a state information calculator 110B instead of the state information calculator 110A represented in FIG. 8. Note that the configuration and operations of each of the components of the calculator excluding the state information calculator 110B and the configuration and operations of each of the components of the image processing device excluding the calculator are the same as those of the second embodiment.

The state information calculator 110B includes a chronological information calculator 111B that calculates chronological information on narrowband images. The chronological information calculator 111B includes an update determination unit 111c that determines the context of update between the latest narrowband image to be used for enhancement and a narrowband image older than the latest narrowband image according to each type.

The update determination unit 111c includes the weight setting unit 1111 that sets a weight used for the enhancement processing and a chronological distance calculator 1112 that calculates chronological distances each between the chronologically first narrowband image and the latest narrowband image of each type. A chronological distance that is calculated by the chronological distance calculator 1112 is a distance based on the time axis and, specifically, is the number of frames between the frame in which each image is updated to the latest one and the chronologically first frame. For example, when the chronologically first frame is the $\lambda_{540}$ image, the chronological distance calculator 1112 calculates the number of frames between the $\lambda_{540}$ image and each of the latest $\lambda_{415}$, $\lambda_{460}$, $\lambda_{540}$ and $\lambda_{630}$ images of the respective types that are stored in the storage 50. The context of update herein refers to the distances each between the narrowband image of each type and the latest narrowband image that varies chronologically. Another method may be used as long as a chronological distance is calculated by the method. For example, elapsed times each of which is a difference between the time at which the latest narrowband image of each type and the time at which the chronologically first narrow and image is captured may be calculated.

The state information calculator 110B multiplies the chronological distances that are calculated by the chronological distance calculator 1112 respectively by the weights that are set for the respective narrowband images, then sums the results of multiplications and uses the sum as the state information. A weight according to Modification 2 of the second embodiment functions as a weighting coefficient for calculating a determination value for determining whether to perform the enhancement processing.

Figure 14:
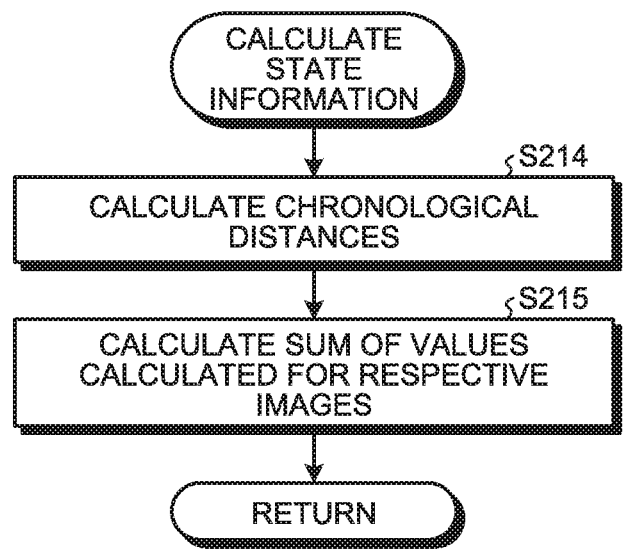
FIG. 14 is a flowchart illustrating a process of calculating state information in Modification 2 of the second embodiment.

The process of calculating state information in Modification 2 of the second embodiment will be described. FIG. 14 is a flowchart illustrating the process of calculating state information in Modification 2 of the second embodiment.

At step S214, the chronological distance calculator 1112 calculates chronological distances each between the narrowband image in the latest frame and each of the latest $\lambda_{415}$, $\lambda_{460}$, $\lambda_{540}$ and $\lambda_{630}$ images of the respective types that are stored in the storage 50.

At step S215 following step S214, the state information calculator 110B multiplies the chronological distances that are calculated by the chronological distance calculator 1112 respectively by weights that are set by the weight setting unit 1111 and that are set for the respective narrow band images and then calculates a sum of the results of the multiplication.

As described above, chronological distances between the narrowband image that is updated in the latest frame and e the $\lambda_{415}$ image, the $\lambda_{460}$ image, the $\lambda_{540}$ image and the $\lambda_{630}$ image that are updated previously may be calculated and, according to state information based on the chronological distances and weights, the setting in the enhancement processing may be changed. When it is determined that the sum is at or under a threshold, the enhanced image creator 120 moves to step S222 in FIG. 11 and, when it is determined that the sum is above the threshold, the enhanced image creator 120 moves to step S223 in FIG. 11.

Third Embodiment

Figure 15:
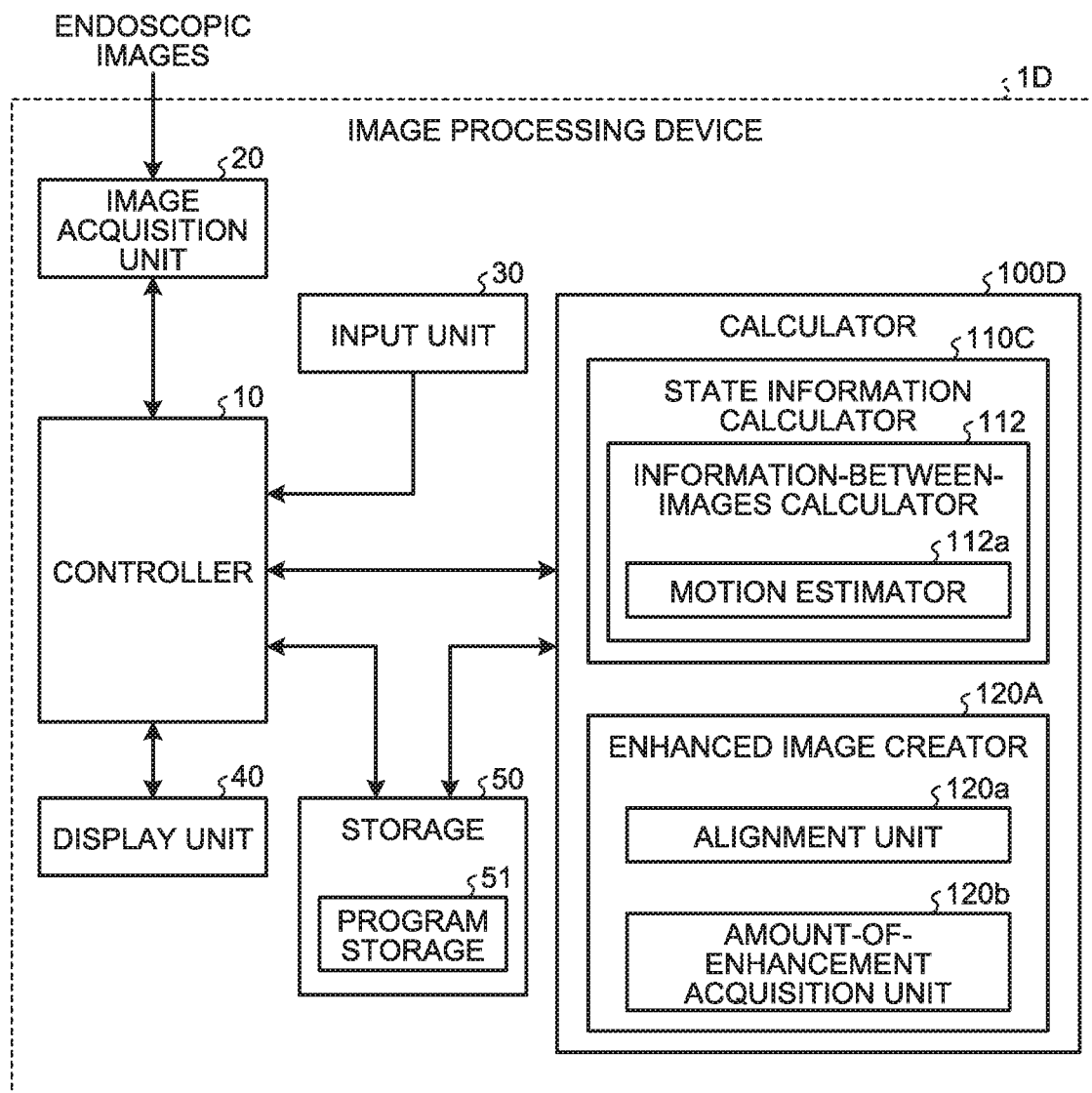
FIG. 15 is a block diagram illustrating a functional configuration of an image processing device according to a third embodiment.

A third embodiment will be described. FIG. 15 is a block diagram illustrating a functional configuration of an image processing device according to the third embodiment. As illustrated in FIG. 15, an image processing device 1D according to the third embodiment includes a calculator 100D instead of the calculator 100A represented in FIG. 6. The image processing device 1D includes a state information calculator 110C instead of the state information calculator 110 represented in FIG. 6. Note that the configuration and operations of each of the components of the calculator excluding the state information calculator 110C and the configuration and operations of each of the components of the image processing device excluding the calculator are the same as those of Example 2 of the first embodiment.

The state information calculator 110C includes an information-between-images calculator 112 that calculates information on differences in an object between a narrowband image to be enhanced and other narrowband images. The information-between-images calculator 112 includes a motion estimator 112a that estimates motions of the object in other narrowband images with respect to that of the narrowband image to be enhanced. The motion estimator 112a, for example, calculates amounts of motion in local areas in an image by block matching and an average of the amounts of motion as the amount of motion. The motion estimator 112a calculates each of amounts of motion between the $\lambda_{540}$ image to be enhanced and the $\lambda_{415}$ image, the $\lambda_{460}$ image and the $\lambda_{630}$ image that are other narrowband images.

The state information calculator 110C calculates a sum of amounts of motion of other narrowband images each of which is calculated by the motion estimator 112a.

Figure 16:
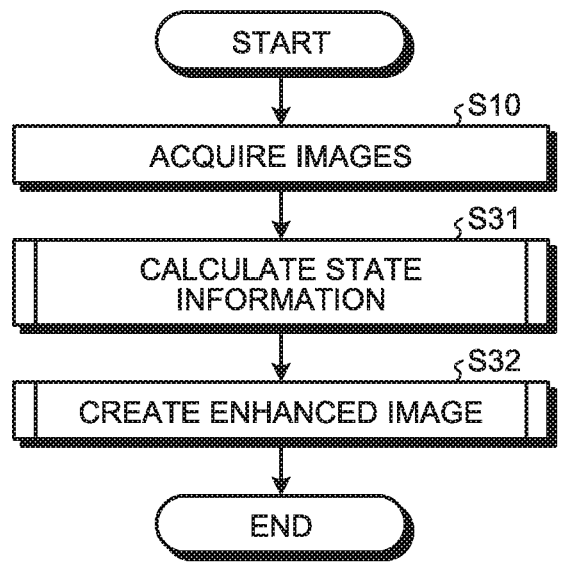
FIG. 16 is a flowchart illustrating image processing that is performed by the image processing device according to the third embodiment.

Operations of the image processing device 1D will be described. FIG. 16 is a flowchart illustrating image processing performed by the image processing device 1D. First of all, at step S10, the image acquisition unit 20 sequentially acquires a $\lambda_{415}$ image, a $\lambda_{460}$ image, a $\lambda_{540}$ image and a $\lambda_{630}$ image that are four narrowband images that are acquired respectively using four narrowband lights whose center wavelengths are 415 nm, 460 nm, 540 nm and 630 nm.

Figure 17:
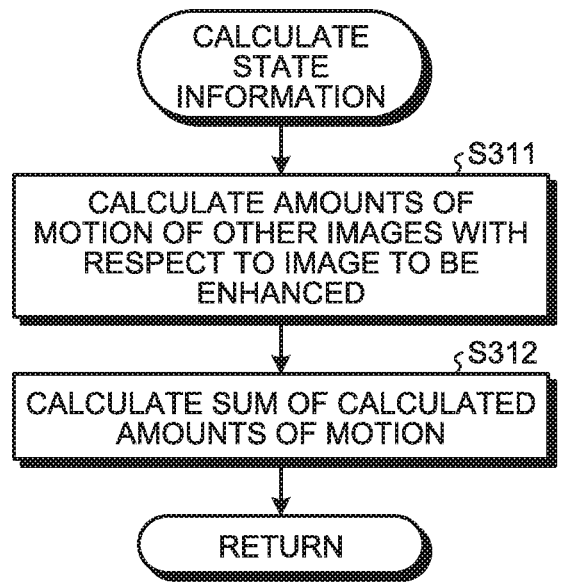
FIG. 17 is a flowchart illustrating a process of calculating state information in the third embodiment.

At the following step S31, the state information calculator 110C calculates state information on a narrowband image. FIG. 17 is a flowchart illustrating a process of calculating state information in the third embodiment.

At step S311, the motion estimator 112a calculates each of amounts of motion between the $\lambda_{540}$ image to be enhanced and the $\lambda_{415}$ image, the $\lambda_{460}$ image and the $\lambda_{630}$ image that are other narrowband images.

At step S312 following step S311, the state information calculator 110C calculates a sum of the amounts of motion of other narrowband images each of which is calculated by the motion estimator 112a.

At the following step S32, the enhanced image creator 120A creates an enhanced image of the $\lambda_{540}$ image. At step S32, the enhanced image creator 120A creates an enhanced image of the $\lambda_{540}$ image according to the flowchart illustrated in FIG. 11. When the determination result represents that the sum is at or under a threshold, the enhanced image creator 120A moves to step S222 in FIG. 11 and, when the determination result represents that the sum is above the threshold, the enhanced image creator 120A moves to step S223 in FIG. 11.

According to the third embodiment described above, according to the motions between the narrowband image to be enhanced and other narrowband images, the enhanced image creator 120A executes any one of performing the enhancement processing on the $\lambda_{540}$ image and causing the current enhanced image to reflect the information on the $\lambda_{540}$ image on which the enhancement processing is performed previously, thereby enabling generation of an appropriate enhanced image according to the acquired images and inhibition of the enhanced image from blurring when the enhancement processing is performed on the image that is displayed in chronological order.

Modification of Third Embodiment

Figure 18:
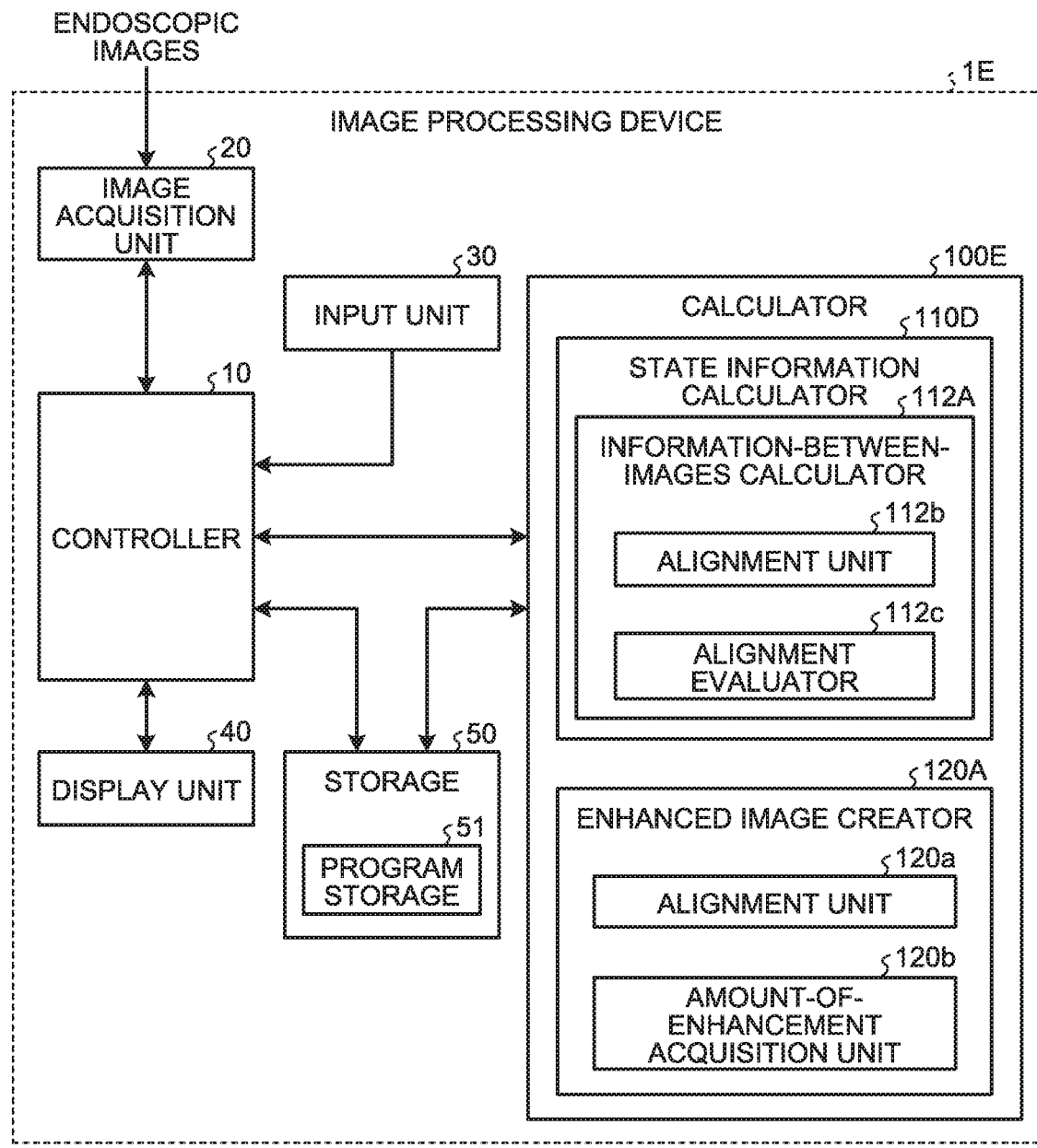
FIG. 18 is a block diagram illustrating a functional configuration of an image processing device according to Modification of the third embodiment.

Modification of the third embodiment will be described. FIG. 18 is a block diagram illustrating a functional configuration of an image processing device according to Modification of the third embodiment. An image processing device 1E according to Modification includes a calculator 100E instead of the calculator 100D represented in FIG. 15. The calculator 100E includes a state information calculator 110D instead of the state information calculator 110C represented in FIG. 15. Note that the configuration and operations of each of the components of the calculator excluding the state information calculator 110D and the configuration and operations of each of the components of the image processing device excluding the calculator are the same as those of the third embodiment.

The state information calculator 110D includes an information-between-images calculator 112A that calculates information between images, that is, information on other narrowband images with respect to a narrowband image to be enhanced. The information-between-images calculator 112A includes an alignment unit 112b that performs alignment between an image and other images that are used for enhancement and an alignment evaluator 112c that calculates an evaluation value representing correctness of a result of alignment.

The alignment unit 112b, for example, estimates an amount of motion of each local area by block matching as in the above-described third embodiment. The alignment unit 112b calculates each of amounts of motion between a $\lambda_{540}$ image to be enhanced and a $\lambda_{415}$ image, a $\lambda_{460}$ image and a $\lambda_{630}$ image that are other narrowband images. The alignment unit 112b then moves the areas in parallel according to the amounts of motion.

The alignment evaluator 112c, for example, calculates each of normalization cross correlations between the images after alignment. Based on the calculated normalization cross correlations, the alignment evaluator 112c calculates an evaluation value that increases as the alignment result becomes preferable. The state information calculator 110D uses the evaluation value that is calculated by the alignment evaluator 112c as state information.

Figure 19:
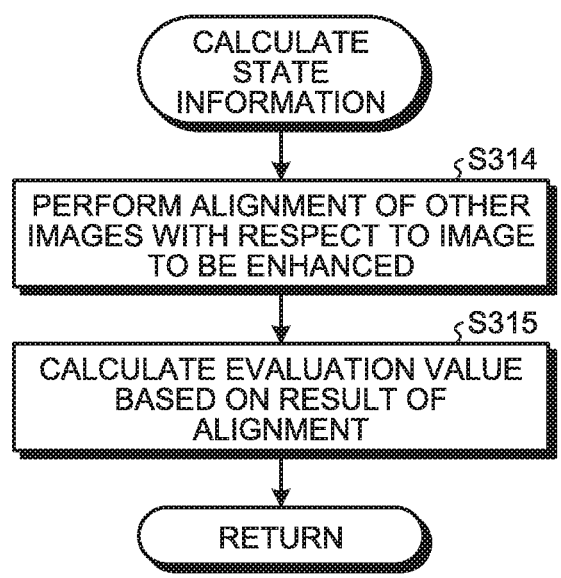
FIG. 19 is a flowchart illustrating a process of calculating state information in Modification of the third embodiment.

A process of calculating state information in Modification of the third embodiment will be described. FIG. 19 is a flowchart illustrating the process of calculating state information in Modification of the third embodiment.

At step S314, the alignment unit 112b performs alignment between an image and other images that are used for enhancement. The alignment unit 112b outputs an alignment result to the alignment evaluator 112c.

At step S315 following step S314, the alignment evaluator 112c calculates an evaluation value representing correctness of the result of alignment. The alignment evaluator 112c calculates an evaluation value that increases as the result of alignment becomes preferable.

Thereafter, the evaluation value and a threshold are compared with each other to create an enhanced image of the $\lambda_{540}$ image along the flowchart illustrated in FIG. 11.

As described above, chronological distances between the narrowband image in the latest frame and the $\lambda_{415}$ image, the $\lambda_{460}$ image, the $\lambda_{540}$ image and the $\lambda_{630}$ image that are updated previously may be calculated and, according to state information based on the chronological distances and weights, the setting in the enhancement processing may be changed.

Other Embodiments

The modes for carrying out the present disclosure have been described; however, the present disclosure should not be limited only to the first to third embodiments described above. For example, the first to third embodiments have been described as one where narrowband images that are acquired using four narrowband lights whose center wavelengths are 415 nm, 460 nm, 540 nm and 630 nm are used. Alternatively, images acquired with lights of types different from one another are usable. Specifically, it suffices if the images are acquired with lights whose distributions of wavelength components, such as center wavelengths, are different form one another. The first to third embodiments have been described as ones where the $\lambda_{540}$ image is displayed in an enhanced manner; however, enhancement and display are not limited thereto. For example, an image of another wavelength band may be enhanced or the enhanced $\lambda_{540}$ image may be combined with an image of another wavelength band to create a display image and the display unit 40 may be caused to display the display image. The present disclosure can include various embodiments that are not described herein.

The present disclosure produces an effect that it is possible to generate an appropriate enhanced image according to images that are acquired.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising
a processor comprising hardware, the processor being configured to:
sequentially acquire multiple images of different types;
determine whether a latest acquired image of the multiple images is of a pre-set type of the different types;
in response to determining that the latest acquired image is of the pre-set type, perform a first enhancement processing on the latest acquired image to generate an enhanced image; and
in response to determining that the latest acquired image is not of the pre-set type, perform a second enhancement processing set a previously generated enhanced image of the pre-set type that is previously generated as the enhanced image.

2. The image processing device according to claim 1, wherein the processor is configured to:
determine whether the latest acquired image of the multiple images contains information to be enhanced in an amount larger than other images of the multiple images; and
in response to determining that the latest acquired image of the multiple images contains the information to be enhanced in the amount larger than other images of the multiple images:
determine differences between the latest acquired image and other images among the multiple images; and
perform a third enhancement processing on an image of the multiple images that is of the pre-set type based on the difference between the latest acquired image and the other images among the multiple images determined.

3. The image processing device according to claim 1, wherein the processor is configured to:
for the latest acquired image of the multiple images:
set a weight for the latest acquired image of the multiple images, wherein a value of the weight set is determined based on an amount of information to be enhanced in the latest acquired image of the multiple images;
determine whether the value of the weight set is at or above a predetermined threshold; and
in response to determining that the value of the weight set is at or above the predetermined threshold, perform a third enhancement processing on an image of the multiple images that is of the pre-set type based on differences between the latest acquired image and other images of the multiple images.

4. The image processing device according to claim 3, wherein the processor is configured to:
for the latest acquired image of the multiple images:
in response to determining that the value of the weight set is below the predetermined threshold and determining that the latest acquired image is of the pre-set type, perform the first enhancement processing on the latest acquired image to generate the enhanced image, wherein the first enhancement processing comprises:
   align the latest acquired image to a previously enhanced image of the pre-set type; and
   enhance the latest acquired image that has been aligned to the previously enhanced image of the pre-set type, based on a previously applied enhancement amount used to enhance the previously enhanced image of the pre-set type.

5. The image processing device according to claim 3, wherein the processor is configured to:
   for the latest acquired image of the multiple images:
      in response to determining that the value of the weight set is below the predetermined threshold and determining that the latest acquired image is not of the pre-set type, perform the second enhancement processing.

6. The image processing device according to claim 1, wherein the processor is configured to:
   for the latest acquired image of the multiple images:
      determine chronological distances between the latest acquired image and each of previously acquired images of the different types;
      perform a multiplication of each of the chronological distances by a weight set for the each of previously acquired images of the different types; and
      calculate a sum of the multiplication of the each of the chronological distances by the weight set for the each of previously acquired images of the different types.

7. The image processing device according to claim 6, wherein the processor is configured to:
   for the latest acquired image of the multiple images:
      determine whether the sum of the multiplication of the each of the chronological distances by the weight set for the each of previously acquired images of the different types is at or under a predetermined threshold; and
      in response to determining that the sum of the multiplication of the each of the chronological distances by the weight set for the each of previously acquired images of the different types is at or under the predetermined threshold, perform a third enhancement processing on an image of the multiple images that is of the pre-set type based on differences between the latest acquired image and other images.

8. The image processing device according to claim 7, wherein the processor is configured to:
   for the latest acquired image of the multiple images:
      in response to determining that the sum of the multiplication of the each of the chronological distances by the weight set for the each of previously acquired images of the different types is above the predetermined threshold and determining that the latest acquired image is of the pre-set type, perform the first enhancement processing on the latest acquired image to generate the enhanced image, wherein the first enhancement processing comprises:
         align the latest acquired image to a previously enhanced image of the pre-set type; and
         enhance the latest acquired image that has been aligned to the previously enhanced image of the pre-set type, based on a previously applied enhancement amount used to enhance the previously enhanced image of the pre-set type.

9. The image processing device according to claim 7, wherein the processor is configured to:
   for the latest acquired image of the multiple images:
      in response to determining that the sum of the multiplication of the each of the chronological distances by the weight set for the each of previously acquired images of the different types is above the predetermined threshold and determining that the latest acquired image is not of the pre-set type, perform the second enhancement processing.

10. The image processing device according to claim 1, wherein the processor is configured to: for the latest acquired image of the multiple images: calculate differences between an object in the latest acquired image and the object in the other images of the multiple images; estimate amounts of motion of the object in the other images of the multiple images with respect to the object in the latest acquired images based on the differences calculated; calculate a sum of the amounts of motion estimated; determine whether the sum of the amounts of motion estimated is at or under a predetermined threshold; and in response to determining that the sum of the amounts of motion estimated is at or under the predetermined threshold, perform a third enhancement processing on an image of the multiple images that is of the pre-set type based on differences between the latest acquired image and other images of the multiple images.

11. The image processing device according to claim 10, wherein the processor is configured to:
   for the latest acquired image of the multiple images:
      in response to determining that the sum of the amounts of motion estimated is above the predetermined threshold and determining that the latest acquired image is of the pre-set type, perform the first enhancement processing on the latest acquired image to generate the enhanced image, wherein the first enhancement processing comprises:
         align the latest acquired image to a previously enhanced image of the pre-set type; and
         enhance the latest acquired image that has been aligned to the previously enhanced image of the pre-set type, based on a previously applied enhancement amount used to enhance the previously enhanced image of the pre-set type.

12. The image processing device according to claim 10, wherein the processor is configured to:
   for the latest acquired image of the multiple images:
      in response to determining that the sum of the amounts of motion estimated is above the predetermined threshold and determining that the latest acquired image is not of the pre-set type, perform the second enhancement processing.

13. The image processing device according to claim 1, wherein the first enhancement processing comprises:
   align the latest acquired image to a previously enhanced image of the pre-set type; and
   enhance the latest acquired image that has been aligned to the previously enhanced image of the pre-set type, based on a previously applied enhancement amount used to enhance the previously enhanced image of the pre-set type.

14. The image processing device according to claim 1, wherein the processor is configured to:

control an image sensor to sequentially capture a plurality of narrowband images, wherein each of the plurality of narrowband images is captured using one of a plurality of narrowband lights having center wavelengths different from one another; and sequentially acquire the plurality of narrowband images as the multiple images of different types.

15. An image processing method comprising:

sequentially acquiring multiple images of different types;

determining whether a latest acquired image of the multiple images is of a pre-set type of the different types;

in response to determining that the latest acquired image is of the pre-set type, performing a first enhancement processing on the latest acquired image to generate an enhanced image; and in response to determining that the latest acquired image is not of the pre-set type, performing a second enhancement processing comprising set a previously generated enhanced image of the pre-set type that is previously generated as the enhanced image.

16. A non-transitory computer readable recording medium on which an executable program is recorded, the program instructing a processor of an image processing device to at least perform:

sequentially acquiring multiple images of different types;

determining whether a latest acquired image of the multiple images is of a pre-set type of the different types;

in response to determining that the latest acquired image is of the pre-set type, performing a first enhancement processing on the latest acquired image to generate an enhanced image; and in response to determining that the latest acquired image is not of the pre-set type, performing a second enhancement processing comprising set a previously generated enhanced image of the pre-set type that is previously generated as the enhanced image.

\* \* \* \* \*